United States Patent
Israel

[19]
[11] Patent Number: 6,136,026
[45] Date of Patent: Oct. 24, 2000

[54] INTRAOCULAR RING

[76] Inventor: Henry M. Israel, 29 Ben Zakai Street, Bnei Brak 51482, Israel

[21] Appl. No.: 09/008,811

[22] Filed: Jan. 20, 1998

[30] Foreign Application Priority Data

Jul. 28, 1997 [IL] Israel ........................................ 121417

[51] Int. Cl.⁷ .................................. A61F 2/14; A61F 2/16
[52] U.S. Cl. ...................................................... 623/4; 623/6
[58] Field of Search ........................................ 623/4, 5, 6

[56] References Cited

U.S. PATENT DOCUMENTS

| | | |
|---|---|---|
| Re. 34,998 | 7/1995 | Langerman . |
| 4,253,199 | 3/1981 | Banko . |
| 4,254,509 | 3/1981 | Tennant . |
| 4,409,691 | 10/1983 | Levy . |
| 4,426,741 | 1/1984 | Bittner . |
| 4,463,458 | 8/1984 | Seidner . |
| 4,464,448 | 8/1984 | Rothfjell . |
| 4,575,373 | 3/1986 | Johnson . |
| 4,790,847 | 12/1988 | Woods . |
| 4,842,601 | 6/1989 | Smith . |
| 4,888,012 | 12/1989 | Horn et al. . |
| 4,892,543 | 1/1990 | Turley . |
| 4,902,293 | 2/1990 | Feaster . |
| 4,963,148 | 10/1990 | Sulc et al. . |
| 4,994,082 | 2/1991 | Richards et al. . |
| 5,047,051 | 9/1991 | Cumming . |
| 5,108,429 | 4/1992 | Wiley . |
| 5,152,789 | 10/1992 | Willis . |
| 5,275,623 | 1/1994 | Sarfarazi . |
| 5,275,624 | 1/1994 | Hara et al. ................................... 623/6 |
| 5,366,501 | 11/1994 | Langerman . |
| 5,476,514 | 12/1995 | Cumming . |
| 5,496,366 | 3/1996 | Cumming . |
| 5,578,082 | 11/1996 | Sussman . |
| 5,593,436 | 1/1997 | Langerman . |
| 5,628,795 | 5/1997 | Langerman ................................. 623/6 |

FOREIGN PATENT DOCUMENTS

| | | |
|---|---|---|
| 0337390 | 10/1989 | European Pat. Off. . |
| 0478929 | 4/1992 | European Pat. Off. . |
| 0507292 | 10/1992 | European Pat. Off. . |
| 0592813 | 4/1994 | European Pat. Off. . |
| 9615734 | 5/1996 | WIPO . |

OTHER PUBLICATIONS

Ronald A. Shachar, "Cause and Treatment of Presbyopia with a Method For Increasing the Amplitude of Accomodation," Ann. Ophthal., 1992; 445–447.

Ronald A. Shachar et al., "Experimental Support for Shachar's Hypothesis of Accomodation", Ann. Ophthal., 1993; 25: 404–409.

Ronald A. Shachar et al., "A Physical Model Demonstrating Shachar's Hypothesis of Accomodation", Ann. Ophthal., 1994; 26:4–9.

D.A. Grinberg, "Questioning Our Classical Understanding of Accomodation and Presbyopia", American Journal of Optometry & Physiological Optics, vol. 63, No. 7, pp. 571–580.

Jane F. Koretz et al., "How the Huma Eye Focuses", Scientific American, Jul. 1988, pp. 64–71.

T. Nagamoto et al., "A Ring to Support Capsular Bag After Continuous Curvilinear Capsulorhexis", J. Cataract Refract Surg. vol. 20, Jul. 1994, pp. 417–420.

*Primary Examiner*—Mickey Yu
*Assistant Examiner*—Dinh X. Nguyen
*Attorney, Agent, or Firm*—Greenblum Bernstein, P.L.C.

[57] ABSTRACT

An intraocular ring for location in a lens capsule having living cells located within a band of a given width extending about a periphery thereof, the ring being formed of a biologically compatible material and being of a width at least as great as said given width.

6 Claims, 5 Drawing Sheets

INTRAOCULAR RING

FIELD OF THE INVENTION

The present invention relates to intraocular optics generally and more particularly intraocular optic mounting rings and to intraocular optic assemblies incorporating such rings.

BACKGROUND OF THE INVENTION

Intraocular optics are well known in the patent literature. A particularly advantageous accommodating intraocular lens implant is described and claimed in applicant's published PCT patent application WO 96/15734, the disclosure of which is hereby incorporated by reference. This published PCT patent application, including specifically the discussion in the Background section thereof, as well as European Patents EP 478929 and 592813, Published European Patent Applications EPA 0507292; EPA 0337390; EPA 0478929; EPA 0592813 and the following U.S. patents are believed to represent the state of the art in the patent literature: U.S. Pat. Nos.5,593,436; 5,578,082; 5,496,366; 5,476,514; 5,366,501; 5,275,624; 5,275,623; 5,152,789; 4,994,082; 4,963,148; 4,902,293; 4,892,543; 4,888,012; 4,842,601; 4,790,847; 4,575,373; 4,464,448; 4,463,458; 4,426,741; 4,409,691; 4,254,509; 4,253,199.

Reference is also made to the following publications in the non-patent literature:

Ronald A. Schachar, CAUSE AND TREATMENT OF PRESBYOPIA WITH A METHOD FOR INCREASING THE AMPLITUDE OF ACCOMMODATION, Ann. Ophthal. 1992; 24:445–452;

Ronald A. Schachar et al, EXPERIMENTAL SUPPORT FOR SCHACHAR'S HYPOTHESIS OF ACCOMMODATION, Ann. Ophthal. 1993; 25:404–409;

Ronald A. Schachar et al, A PHYSICAL MODEL DEMONSTRATING SCHACHAR'S HYPOTHESIS OF ACCOMMODATION, Ann. Ophthal. 1994; 26:4–9;

D. A. Grinberg, QUESTIONING OUR CLASSICAL UNDERSTANDING OF ACCOMMODATION AND PRESBYOPIA, American Journal of Optometry & Physiological Optics, Vol. 63, No. 7, pp. 571–580.

The use of a ring for supporting the capsular bag after continuous curvilinear capsulorhexis and for preventing aftercataract is described in U.S. Pat. No. 5,275,624, European Published Patent Application EP 0507292 A1 and in the following publication:

A ring to support the capsular bag after continuous curvilinear capsulorhexis, by T. Nagamoto et al, J. Cataract Refract Surg, Vol. 20, July, 1994, pp 417–420.

The rings proposed in the foregoing publications range in width from 0.3 to 1.0 mm and in thickness from 0.4 mm to 2.0 mm.

SUMMARY OF THE INVENTION

The present invention seeks to provide an improved intraocular ring and an optic assembly including such ring, which, by virtue of its width dimensions inhibits cell growth and kills existing cells at the equator of the lens capsule.

There is thus provided in accordance with a preferred embodiment of the present invention an intraocular ring for location in a lens capsule having living cells located within a band of a given width extending about a periphery thereof, the ring being formed of a biologically compatible material and being of a width at least as great as said given width.

There is also provided in accordance with a preferred embodiment of the present invention an intraocular optic assembly including an intraocular optic, a ring for location in a lens capsule having living cells located within a band of a given width extending about a periphery thereof, the ring being formed of a biologically compatible material and being of a width at least as great as said given width, and haptics for mounting the intraocular optic.

There is also provided in accordance with a preferred embodiment of the present invention a method for inhibiting cell growth about an implanted optic comprising providing an intraocular ring in a lens capsule having living cells located within a band of a given width extending about a periphery thereof, the ring being formed of a biologically compatible material and being of a width at least as great as said given width, and mounting an implanted optic within the lens capsule. The biologically compatible material may be, for example, hyaluronic acid (including the sodium, potassium and other salts thereof), polymethylmethacrylate (PMMA), silicone, collagen, hydrogel and the like.

The ring may be a closed ring or alternatively may be an open ring, preferably in an at least particularly overlapping arrangement. The ring may be formed of latex.

In accordance with a preferred embodiment of the present invention, the ring has a width of at least 1.5 mm and preferably at least 2.5 mm.

For the purposes of the present specification and claims, width of the ring refers to the width of the ring in its relaxed state, prior to any curvature being applied thereto after insertion in the capsule.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
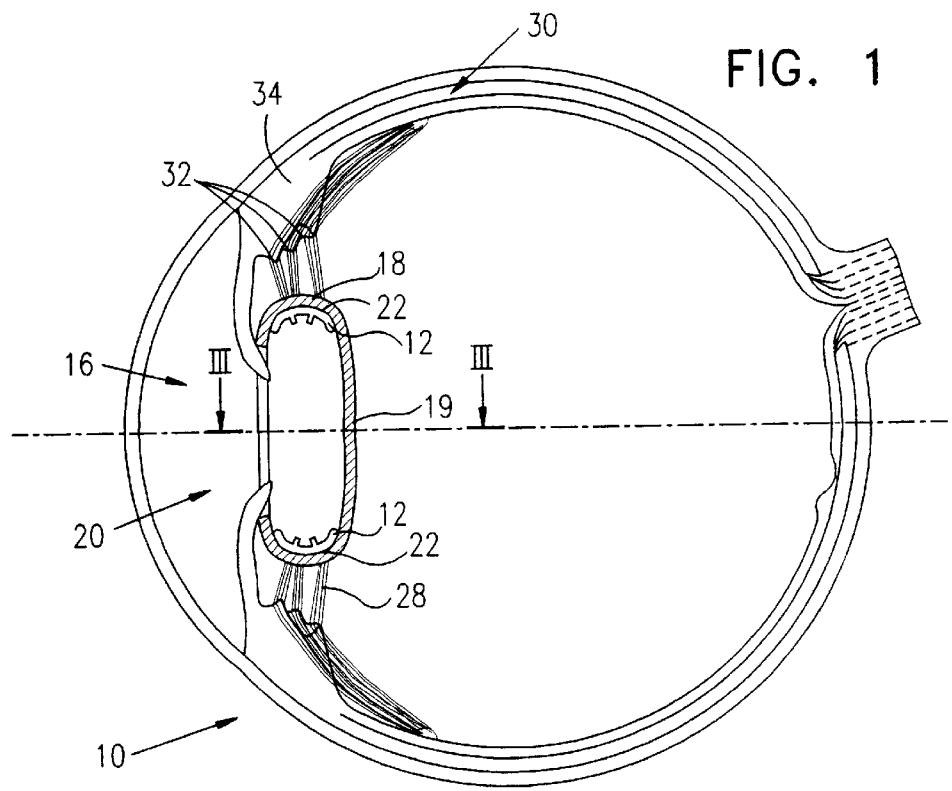
FIG. 1 shows a cross-sectional view of an eye having therein a lens capsule containing an intraocular ring constructed and operative in accordance with a preferred embodiment of the invention.

FIG. 1 shows a cross-section of a human eye 10 having an intraocular ring 12, in accordance with a preferred embodiment of the invention, installed in place of the original material in a lens capsule 16. In this and all other cross-sectional diagrams of the eye and structures therein, the cornea and other anterior portions of the eye are at the left of the figure, and the retina and posterior portions of the eye are to the right.

Lens capsule 16, from which the original lens material has been removed, includes an outer edge 18, which is left intact and, optionally, a posterior wall 19 at least a portion of which may be left intact. At least a portion of the original anterior wall of the capsule is generally removed during the operation for removal of the lens material leaving an opening 20, through which the intraocular ring 12 and normally an intraocular lens system (not shown) is installed.

The outer edge 18 of the capsule is termed the "equator". Normally there is present along an interior surface of the equator a band of living cells 22. It is a particular feature of the present invention that the width of intraocular ring 12 is sufficient to overlie the band of living cells 22 with sufficient margin as to suffocate such cells, thereby preventing cell growth onto an intraocular optic system inserted into the capsule and to kill existing cells in band 22.

Figure 3B:
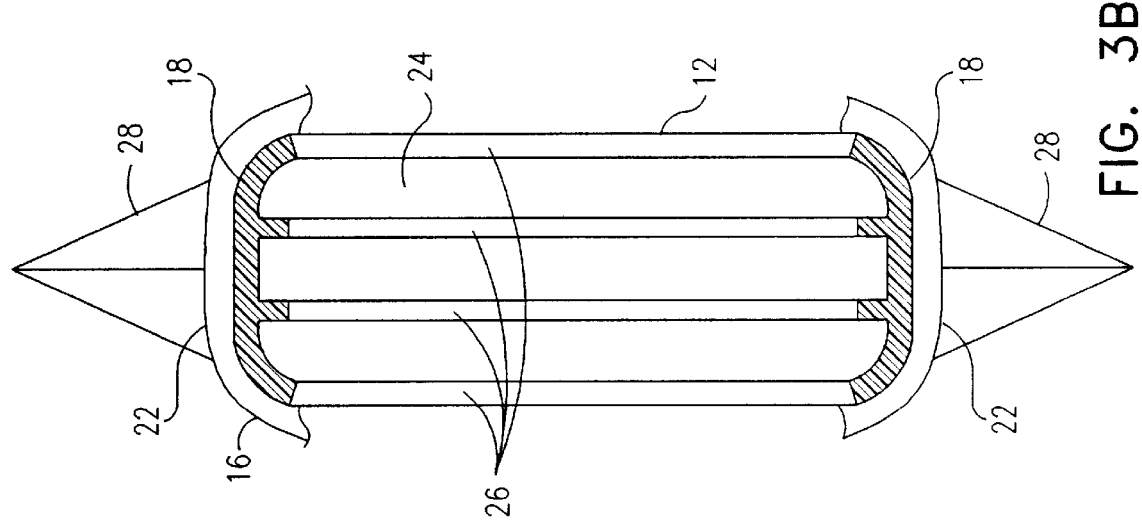
FIGS. 3A and 3B are sectional illustrations of the intraocular ring of FIG. 1, taken along lines III—III in FIG. 1 respectively prior to and following insertion in the capsule.
Figure 3A:
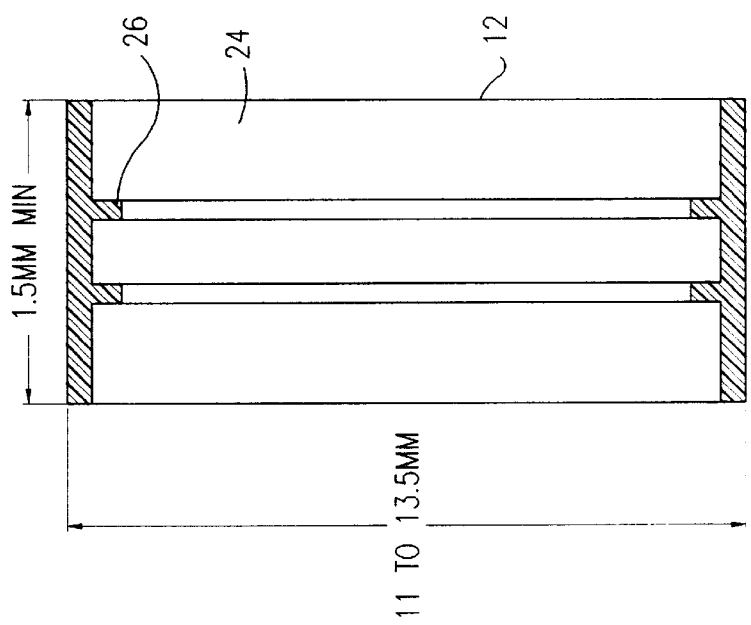

As shown more clearly in FIGS. 3A and 3B, intraocular ring 12 includes a generally cylindrical portion 24 and a pair of spaced ribs 26 for providing structural support to cylindrical portion 24. As seen particularly in FIG. 3B, upon insertion of the ring 12 in the capsule 16, the capsule tends to bend the outer edges of the cylindrical portion 24 inwardly.

As shown in FIG. 3B, one end of zonular fibers 28, also known as zonules, is attached to edge 18 of lens capsule 16. As seen in FIG. 1, the other end of the zonules is attached to the sclera 30 of the eye. Intermediate their ends, the zonular fibers are acted upon by ligaments or the like 32 which are controlled by ciliary muscle 34. The portion of the eye comprising the ciliary muscle and the volume it encloses is also known as the ciliary body.

Figure 4B:
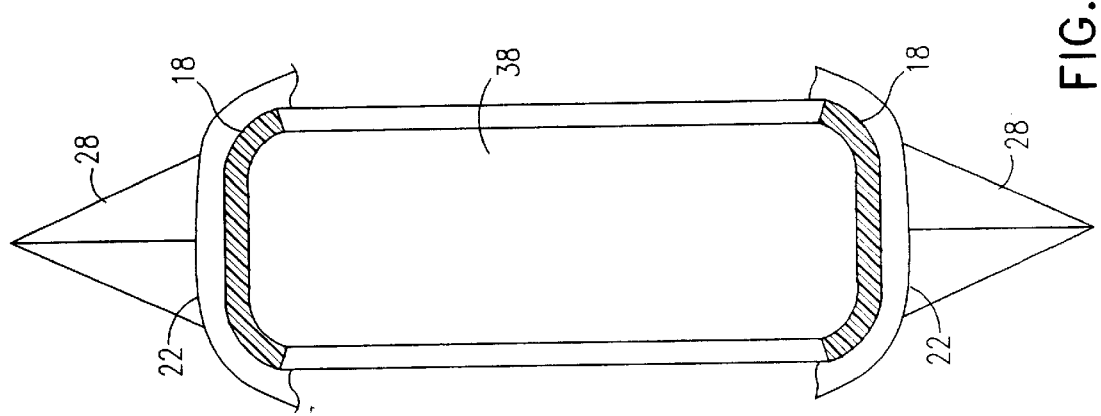
FIGS. 4A and 4B correspond to FIGS. 3A and 3B and show an alternative configuration of intraocular ring.
Figure 4A:
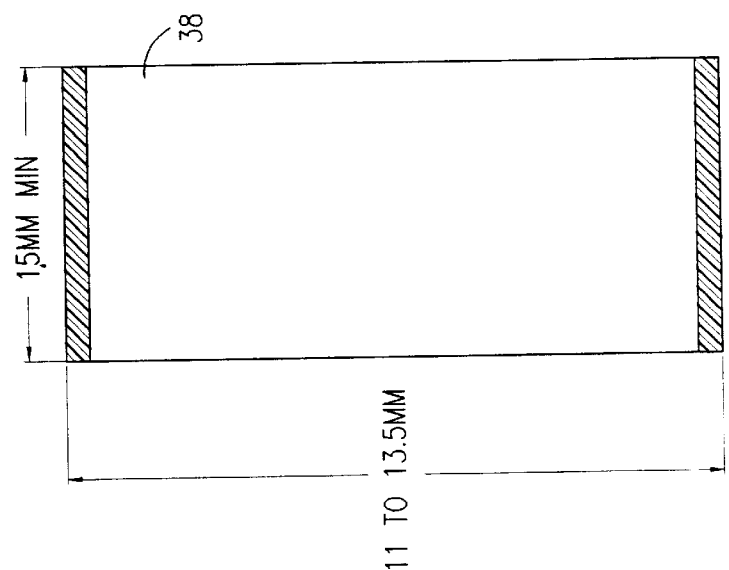

FIGS. 4A and 4B correspond to FIGS. 3A and 3B and illustrate an alternative ring configuration which may be identical to that of FIGS. 3A and 3B, with the elimination of ribs 26. Thus, it can be seen from a consideration of FIGS. 4A and 4B that the ring comprises a generally cylindrical portion 38, at least a portion of which is typically somewhat thicker than the corresponding cylindrical portion 24 of the ring of FIGS. 3A and 3B.

Figure 2:
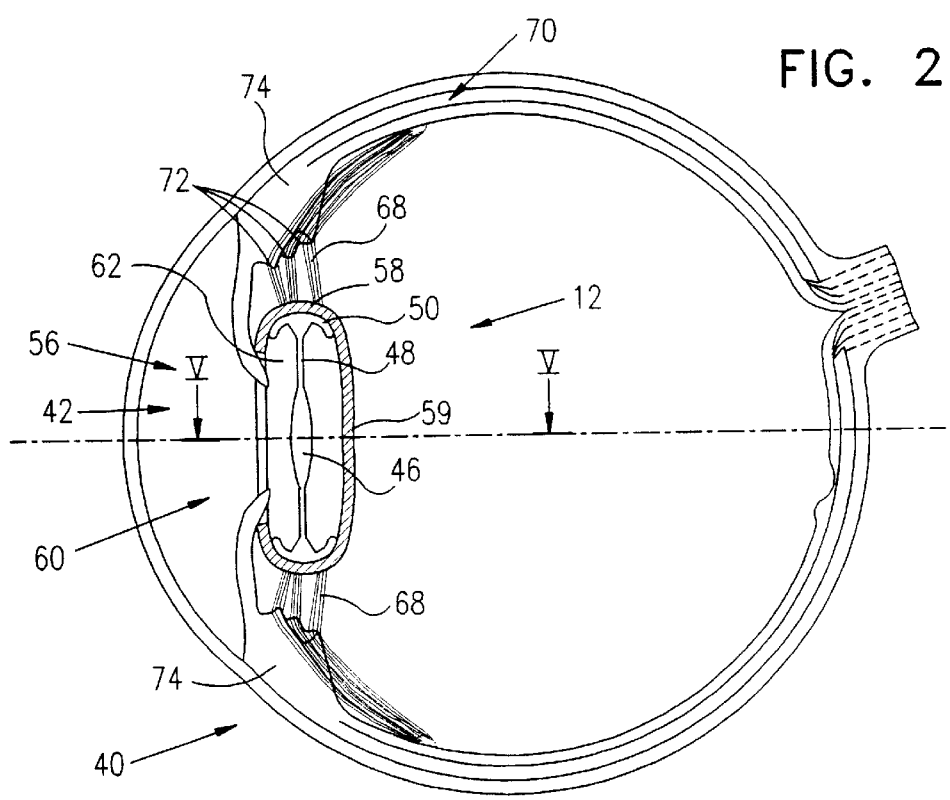
FIG. 2 shows a cross-sectional view of an eye having therein a lens capsule containing an intraocular optic assembly constructed and operative in accordance with a preferred embodiment of the invention.

FIG. 2 shows a cross-section of a human eye 40 having an integrated intraocular lens system 42, in accordance with a preferred embodiment of the invention, installed in place of the original material in a lens capsule 56.

Figure 5B:
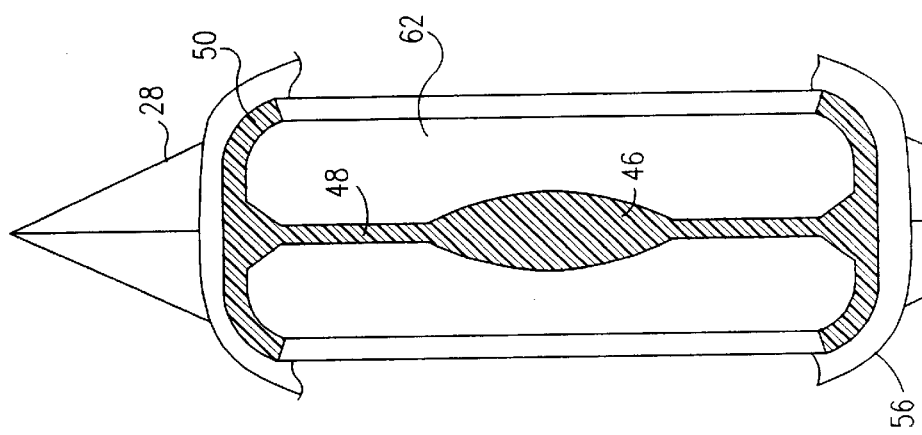
FIGS. 5A and 5B are sectional illustrations of the intraocular optic assembly of FIG. 2, taken along lines V—V in FIG. 2 respectively prior to and following insertion in the capsule.
Figure 5A:
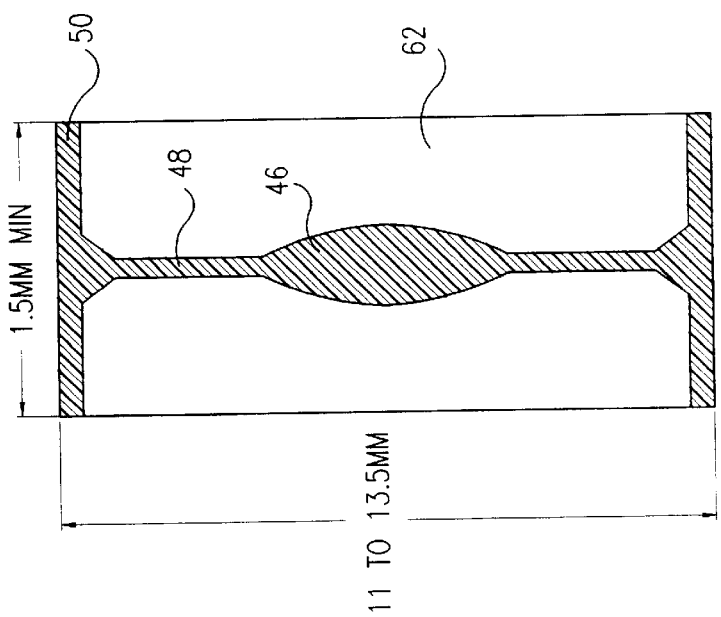
Figure 5C:
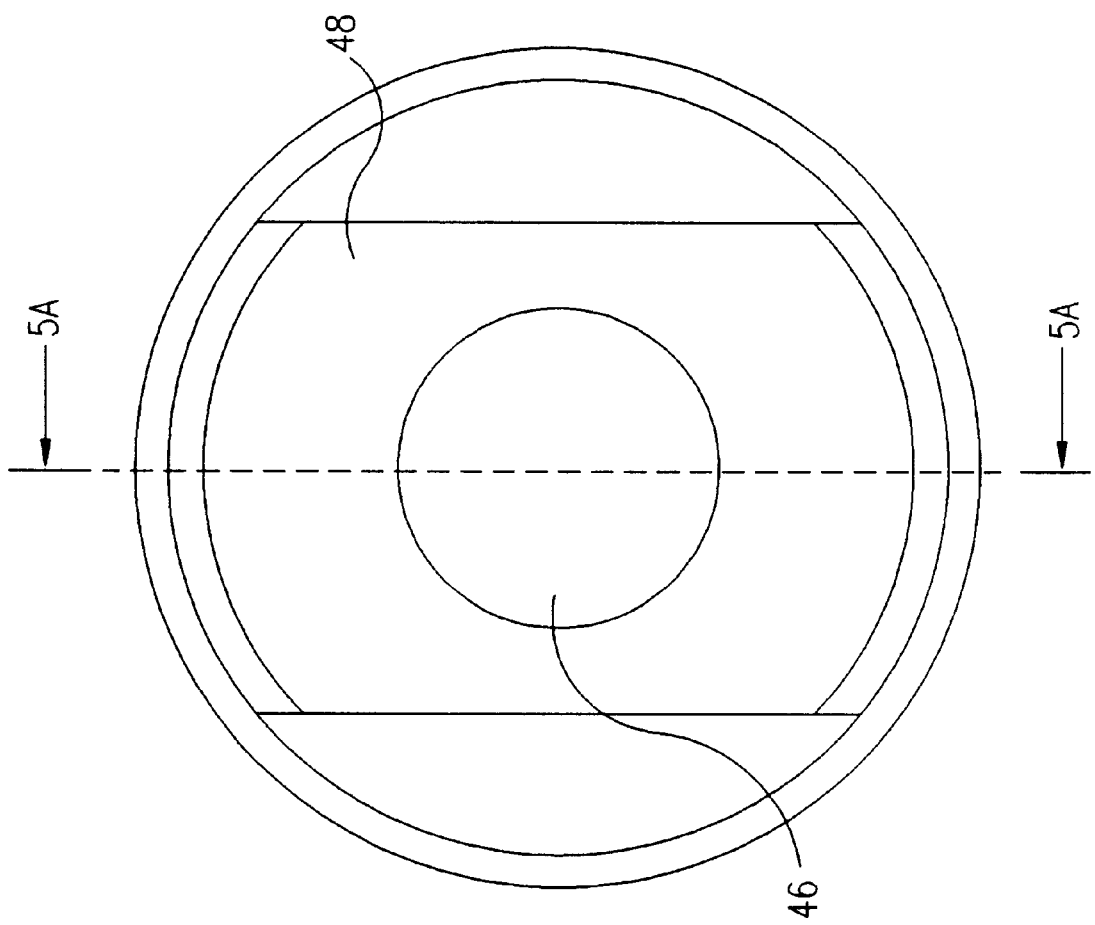
FIG. 5C is a planar view of the intraocular optic assembly of FIGS. 5A and 5B.

As seen in FIGS. 5A–5C, intraocular lens system 42 comprises an optic 46 mounted via integrally formed haptics 48 on an intraocular ring 50, all preferably formed as one piece and placed within lens capsule 56. Lens capsule 56, from which the original lens material has been removed, includes an outer edge 58, which is left intact and, optionally, a posterior wall 59 at least a portion of which may be left intact. At least a portion of the original anterior wall of the capsule is generally removed during the operation for removal of the lens material leaving an opening 60, through which the lens system is installed.

Ring 50 preferably comprises a cylindrical portion 62, from interior central surface locations thereof extend haptics 48 which support optic 46. As seen particularly in FIG. 5B, insertion of the ring 50 in the capsule 56, tends to bend the outer edges of the cylindrical portion 62 inwardly.

As shown in FIG. 2, one end of zonular fibers 68, also known as zonules, is attached to edge 58 of lens capsule 56. The other end of the zonules is attached to the sclera 70 of the eye. Intermediate their ends, the zonular fibers are acted upon by ligaments or the like 72 which are controlled by ciliary muscle 74. The portion of the eye comprising the ciliary muscle and the volume it encloses is also known as the ciliary body.

The intraocular lens system may be formed as one piece from plural materials or reinforced, so as to cause various portions thereof to have greater or lesser rigidity.

It will be appreciated by persons skilled in the art that the present invention is not limited to what has been particularly shown and described hereinabove. Rather the scope of the present invention includes both combinations and subcombinations of the features described hereinabove as well as variations and modifications thereof which would occur to a person of skill in the art upon reading the foregoing description, and which are not in the prior art.

What is claimed is:

1. An intraocular ring for location in a lens capsule having living cells located within a band of a given width extending about a periphery thereof, the ring being formed of a biologically compatible material and being of a width at least 2.5 mm, the ring comprising a generally cylindrical portion and at least one annular rib extending radially inwardly from said cylindrical portion.

2. The intraocular ring according to claim 1 and comprising a plurality of said annular ribs.

3. The intraocular ring according to claim 2 and wherein said ribs are spaced from each other.

4. The intraocular ring according to claim 1 and wherein said at least one annular rib comprises a haptic which supports an optic.

5. The intraocular ring according to claim 1 and wherein said biologically compatible material is sufficiently flexible such that outer edges of said cylindrical portion bend inwardly upon installment of said ring in said lens capsule.

6. The ring according to claim 1 wherein said ring is made of latex.

\* \* \* \* \*